US008658129B2

(12) United States Patent
Zhang et al.

(10) Patent No.: US 8,658,129 B2
(45) Date of Patent: Feb. 25, 2014

(54) AGENTS AND METHODS FOR THE IMAGING OF MYELIN BASIC PROTEIN

(75) Inventors: Rong Zhang, Niskayuna, NY (US); Tiberiu Mircea Siclovan, Rexford, NY (US); Cristina Abucay Tan Hehir, Niskayuna, NY (US); Victoria Eugenia Cotero, Watervilet, NY (US); Bruce Fletcher Johnson, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 292 days.

(21) Appl. No.: 13/031,349

(22) Filed: Feb. 21, 2011

(65) Prior Publication Data

US 2011/0142759 A1    Jun. 16, 2011

Related U.S. Application Data

(63) Continuation-in-part of application No. 12/478,300, filed on Jun. 4, 2009, and a continuation-in-part of application No. 12/694,820, filed on Jan. 27, 2010, now abandoned.

(51) Int. Cl.
| | |
|---|---|
| *A61K 49/00* | (2006.01) |
| *A61K 49/10* | (2006.01) |
| *A61K 51/04* | (2006.01) |
| *A61K 101/02* | (2006.01) |
| *A61B 5/00* | (2006.01) |
| *A61B 5/055* | (2006.01) |

(52) U.S. Cl.
USPC ......... 424/1.65; 424/1.81; 424/1.89; 424/9.1; 424/9.3; 424/9.37; 424/9.6; 600/420

(58) Field of Classification Search
None
See application file for complete search history.

(56) References Cited

U.S. PATENT DOCUMENTS

| 4,511,651 A * | 4/1985 | Beaty et al. ............ 435/15 |
| 5,324,718 A * | 6/1994 | Loftsson ................ 514/58 |
| 6,229,024 B1 | 5/2001 | Schmued |
| 6,372,451 B1 | 4/2002 | Schmued |
| 7,250,525 B2 * | 7/2007 | Kung et al. ............. 556/81 |
| 7,261,770 B2 * | 8/2007 | El-Shoubary et al. ...... 106/499 |
| 2003/0232016 A1 | 12/2003 | Heinrich |
| 2006/0021939 A1 * | 2/2006 | Mallet et al. ........... 210/656 |
| 2007/0028032 A1 | 2/2007 | Baba |

FOREIGN PATENT DOCUMENTS

WO    WO2009029936 A1    3/2009

OTHER PUBLICATIONS

Stankoff et al. Imaging of CNS myelin by positron-emission tomography. 2006 Proc. Natl. Acad. Sci. USA 103: 9304-9309.*
Sun et al. Two-photon absorption properties of multi-branched bis-(styryl)benzene based organic chromophores. 2004 J. Mol. Struct. (Theochem) 682: 185-189.*
Monici M. Cell and tissue autofluorescence research and diagnostic applications. 2005 Biotechnol. Annu. Rev. 11 : abstract only.*
Wu et al., "A Novel Fluorescent Probe That is Brain Permeable and Selectively Binds to αMyelin", Journal of Histochemistry & Cytochemistry, vol. 54, No. 9, pp. 997-1004, 2006.
Fridkis-Hareli et al., Direct Binding of Myelin Basic Protein and Synthetic Copolymer 1 to Class II Major Histocompatibility Complex Molecules on Living Antigen-Presenting Cells—Specificity and Promiscuity, Proc. Natl. Acad. Sci., vol. 91, pp. 4872-4876, May 1994.
Wu et al., Molecular Probes for Imaging Myelinated white Matter in CNS, J. Med. Chem., vol. 51, No. 21, pp. 6682-6688, 2008.
Xiang et al., "Detection of Myelination Using a Novel Histological Probe", Journal of Histochemistry & Cytochemistry, vol. 53, No. 12, pp. 1511-1516, 2005.
Co-pending US Patent Application entitled "Myelin Detection Using Benzofuran Derivatives", U.S. Appl. No. 12/211,254, filed Sep. 17, 2008.
Co-pending US Patent Application entitled "Annulus Fibrosus Detection in Intervertebral Discs Using Molecular Imaging Agents", U.S. Appl. No. 12/370,207, filed Feb. 12, 2009.
Herrmann et al., "Synthesis of Water-Soluble Phosphines and Their Transition Metal Complexes", Inorganic Synthesis, vol. 32, pp. 8-25, 1998.

* cited by examiner

*Primary Examiner* — Michael G Hartley
*Assistant Examiner* — Jennifer Lamberski
(74) *Attorney, Agent, or Firm* — Eileen B. Gallagher

(57) ABSTRACT

The present invention relates to agents capable of binding to myelin basic protein in a subject. Also provided are methods for the detection of myelin-associated neuropathy comprising identifying a subject at risk of or diagnosed with a myelin-associated neuropathy, administering to a subject an agent that binds specifically to myelin basic protein, and determining myelination in the subject by detecting the agent present in the subject. A kit containing the agent or its derivatives for use in detecting myelin basic protein is also provided.

18 Claims, 4 Drawing Sheets

Agent 5

Agent 3

AGENTS AND METHODS FOR THE IMAGING OF MYELIN BASIC PROTEIN

CROSS-REFERENCE TO RELATED APPLICATIONS

This application is a continuation-in-part to U.S. patent application Ser. Nos. 12/478,300 filed Jun. 4, 2009 and 12/694,820 filed Jun. 27, 2010; the disclosures of which are incorporated herein by reference in their entirety.

STATEMENT REGARDING FEDERALLY SPONSORED RESEARCH & DEVELOPMENT

This invention was made with Government support under contract number 1R01EB011872-01 awarded by the National Institute of Health. The Government has certain rights in the invention.

BACKGROUND

Information flow within the nervous system requires the perpetuation of ionic gradients along neurons. In many neurons, effective and efficient perpetuation of such gradients along axons requires electrical insulation. Myelin, a lipid-rich, dielectric substance that ensheathes axons, serves this insulating function. The nervous system contains high levels of myelin, which is especially enriched where many myelinated axons are bundled together, such as in tracts of the spinal cord and spinal nerve roots, nerves in the peripheral nervous system, and fiber tracts in the brain, collectively called "white matter", as opposed to "grey matter". Because non-nervous system tissue lacks myelin, the presence of myelin can distinguish nerve tissue from other tissue types; the spinal cord and spinal nerve roots from non-nervous elements of the vertebral column, and white matter from grey matter in the brain.

The ability to qualitatively or quantitatively visualize myelin, either in vivo or in vitro, confers upon researchers and clinicians important diagnostic and treatment tools. For example, the ability to visually identify peripheral nerves during open or minimally invasive surgery assists surgeons in avoiding cutting or damaging nerves. Previous efforts in image-guided surgery of nerves utilized modalities that would not require contrast agents or fluorescent labeling of axons by retrograde transport. A challenge in the first approach is that the signal is typically ambiguous Retrograde labeling of nerves in animal models is widely reported in the literature. Although this strategy may work, there are many inherent problems. Labeling would depend on exactly where the contrast agent is injected. If the nerves fail to take up the contrast agent, the nerve would not be visualized. In some cases, nerve stimulation is required to facilitate retrograde transport. The long times required for retrograde transport may not be clinically feasible.

Myelinated nerves and fiber tracts serve as useful landmarks in anatomical studies carried out by preclinical and basic neuroscience researchers. Furthermore, the formation of myelin sheaths is an important step in the generation and functional stability of new neurons; so the availability of myelin markers may aid researchers study such processes. Myelin-labeling methodologies are also useful in the development of numerous therapies, neural stem cell research, and putative animal models of myelin-associated neuropathies. In vivo myelin imaging of the spinal cord assists clinicians in the diagnosis and treatment of spinal cord pathology, such as nerve compression or herniated discs as well as myelin-associated neuropathies, such as multiple sclerosis which results in damage to myelin within the central or peripheral nervous system, or Alzheimer's disease which could result in modification in myelination pattern in the brain. The ability to measure amounts of myelination in vivo in patients with such conditions would aid clinicians and researchers in diagnosing and prognosing myelin-associated neuropathies.

The spinal nerve roots can be damaged as they traverse the spinal canal, but are especially vulnerable in the intervertebral foramen, where the spinal nerve roots join to form the spinal nerves. Syndromes such as cervical radiculopathy, sciatica, intervertebral disc herniation, and root compression are caused by compression primarily from tumors or other lesions, which usually present with back or neck pain. Back or neck pain may be caused by a variety of musculoskeletal mechanisms and the physician needs to be able to examine the nervous system to determine if there is compression of nerve roots or the spinal cord. The ability to image and identify the source of chronic neck or back pain could enable surgeons to effectively treat these syndromes.

Myelin is a protein and lipid-rich matrix formed by oligodendrocytes in the central nervous system (CNS) and Schwann cells in the peripheral nervous system (PNS). Because two different cell types in CNS and PNS produce myelin, namely oligodendrocytes and Schwann cells respectively, there are similarities and differences in protein and lipid composition depending on the source of myelin. In both instances, myelin is composed of about 80% lipid fraction and about 20% protein fraction. Numerous studies have examined the molecular components of both fractions.

The lipid fraction in myelin contains cholesterol, cholesterol ester, cerebroside, sulfatide, sphingomyelin, phosphotidylethanolomine, phosphotidylcholine, phosphotidylserine, phosphotidylinositol, triacylglycerol, and diacylglycerol. The protein fraction is composed of several proteins, which include myelin basic protein (MBP), peripheral myelin protein 22 (PMP22), connexin 32 and myelin-associated glycoprotein (MAG), which are, produced by both PNS and CNS cells; the protein myelin protein zero (MPZ), produced by the PNS only; and proteolipid protein, produced by CNS cells only.

MBP is a major protein component of myelin at 5%-15%, which translates into about 5 mM concentration of MBP. Techniques such as circular dichroism, NMR and EPR spectroscopy, atomic force microscopy and others, suggest that MBP may have a compact C-shaped form with a core element of beta-sheet structure, but only when associated with lipids. The interaction of myelin basic protein to lipids can cause conformational variability and may be critical for function.

An agent that selectively binds to MBP may result in improvements in myelin staining and thereby aid in nerve visualization. Nerve visualization may be further improved through elimination of unbound and nonspecifically bound dye, and improved optical properties to allow enhanced contrast between myelin and surrounding tissue.

Furthermore, labeling agents, which may have high aqueous solubility, may lessen nonspecific partitioning of the agent to the non-target tissue, such as adipose tissue. Also, high aqueous solubility may enable the agents to be formulated in a pharmaceutical carrier with less or no known toxic effects. For systemic circulation, increased aqueous solubility of the agents may also enhance their bioavailability and kinetics of binding and clearance.

BRIEF DESCRIPTION

Provided herein are agents capable of binding myelin-basic protein. In one embodiment an agent comprises a compound of Formula I a salt thereof

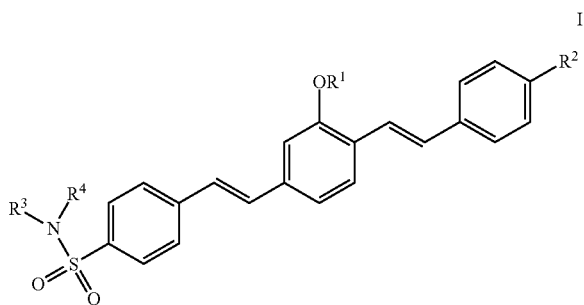

wherein $R^1$ is an alkyl group, $R^2$ is an electron donating group, and $R^3$ and $R^4$ are independently a hydrogen, alkyl, substituted alkyl, amine, or substituted amine group. In certain embodiments, R3 and R4 may also form a ring structure such as alkyl or alkoxyl substituted piperidine, piperazine, or morpholine.

In one embodiments methods for the detection of myelin-associated neuropathy are provided comprising identifying a subject at risk of or diagnosed with a myelin-associated neuropathy, administering to a subject the aforementioned agent that binds specifically to myelin basic protein, and determining myelination in the subject by detecting the agent present in the subject.

In one embodiment a method of imaging myelin basic protein in a surgical field is provided comprising the steps of contacting the surgical site with the agent, and detecting the agent present in an open surgical setting or in a minimally invasive surgical setting.

In another embodiment a kit for detecting myelin-associated neuropathy in a subject is provided, the kit comprising an agent at binds specifically to myelin basic protein and a pharmaceutically acceptable carrier.

BRIEF DESCRIPTION OF THE FIGURES

These and other features, aspects, and advantages of the present invention will become better understood when the following detailed description is read with reference to the accompanying figures wherein.

DETAILED DESCRIPTION

Figure 1:
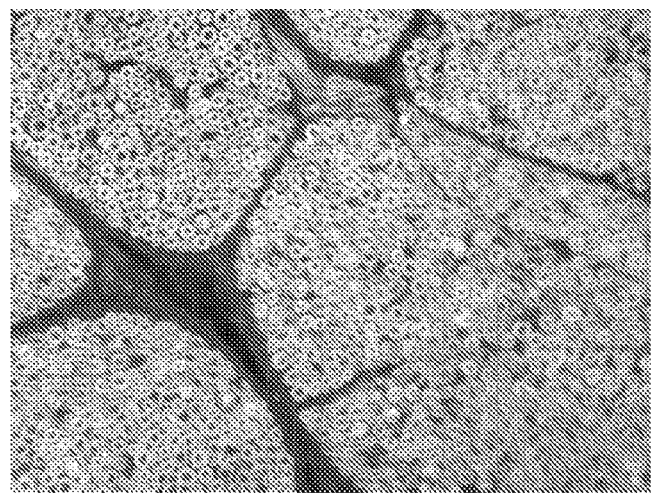
FIG. 1 shows results from ex vivo staining of rat trigeminal nerve sections (bottom) by sulfonamide agents (1), (2), and (3).
Figure 1:
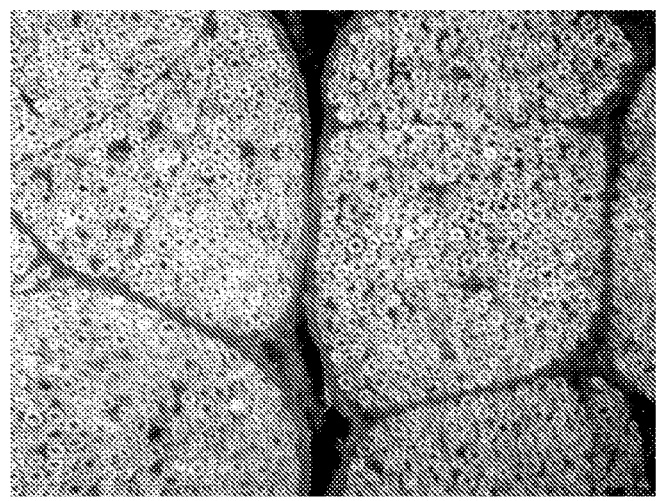
Figure 1:
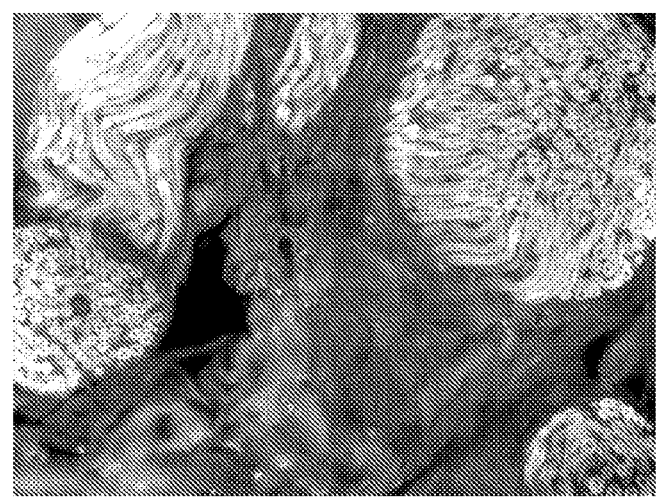

The following detailed description is exemplary and not intended to limit the invention of the application and uses of the invention. Furthermore, there is no intention to be limited by any theory presented in the preceding background of the invention or descriptions of the drawings.

Definitions

To more clearly and concisely describe and point out the subject matter of the claimed invention, the following definitions are provided for specific terms, which are used in the following description and the appended claims.

"Myelin-associated neuropathy" generally refers to any condition in which the insulating material ensheathing portions of neuronal cells becomes damaged or dysfunctional as a component of a syndrome, disease, or other pathological condition, such as, but not limited to, multiple sclerosis, Guillain-Barré syndrome, leukodystrophies, metachromatic leukodystrophy, Refsum's disease, adrenoleukodystrophy, Krabbe's disease, phenylketonuria, Canavan disease, Pelizaeus-Merzbacher disease, Alexander's disease, diabetic neuropathy, chemotherapy induced neuropathy, Alzheimer's disease, vascular dementia, dementia with Lewy bodies, or any combination thereof.

"Agent" refers to a solution or carrier for introducing a compound into a subject in a manner to allow the compound to be administered at a desired concentration and efficacy. The agent may include, but is not limited to, solvents, stabilization aids, buffers, and fillers. A pharmaceutical agent refers to the agents having medicinal or other biological properties including, but not limited to, use in therapy or diagnostics.

An agent exhibits "specific binding" for myelin if it associates more frequently with, more rapidly with, for a longer duration with, or with greater affinity to, myelin than with tissues not containing myelin. "Non-specific binding" refers to binding of the agent to non-myelin containing tissue. For relative binding values, such as specific binding or non-specific binding, each sample should be measured under similar physical conditions (i.e., temperature, pH, formulation, and mode of administration). Generally, specific binding is characterized by a relatively high affinity of an agent to a target and a relatively low to moderate capacity. Typically, binding is considered specific when the affinity constant $K_a$ is at least $10^6$ $M^{-1}$. A higher affinity constant indicates greater affinity, and thus typically greater specificity. For example, antibodies typically bind antigens with an affinity constant in the range of $10^6$ $M^{-1}$ to $10^9$ $M^{-1}$ or higher. "Non-specific" binding usually has a low affinity with a moderate to high capacity. Non-specific binding usually occurs when the affinity constant is below $10^6$ $M^{-1}$. Controlling the time and method used to contact the agent with the tissues reduces non-specific binding.

"Washing" generally refers to any method, such as but not limited to, immersion in, or flushing by repeated application of, a non-labeling solution or other substance, such as but not limited to water, saline, buffered saline, or ethanol, so as to provide a medium for dissociation, dispersal, and removal of unbound or non-specifically bound labeling compound from non-myelinated components of the tissue or sample of tissue without eliminating specific binding to myelin.

"Baseline fluorescence" refers to the frequency and magnitude of electromagnetic radiation emitted by a tissue or sample of tissue upon being exposed to an external source of electromagnetic radiation in the absence of administration or binding of any fluorescing compound, as distinguished from the radiation emitted following the administration and binding of such fluorescing compound and exposure to an external source of electromagnetic radiation.

"Control sample representative of the tissue section" refers to a tissue sample of a similar size, morphology, or structure as the tissue sample to be analyzed, and with a level of myelin whereby the sample's level of myelin serves as a reference to which other samples' myelin levels may be compared.

"Parenteral administration" refers to any means of introducing a substance or compound into a subject, that does not involve oral ingestion or direct introduction to the gastrointestinal tract, including but not limited to subcutaneous injection, intraperitoneal injection, intramuscular injection, intravenous injection, intrathecal injection, intracerebral injection, intracerebroventricular injection, intraspinal injection, intrathecal injection, intracerebral injection, intracerebroventricular injection, or intraspinal injection or any combination thereof.

"Pharmaceutical carrier" refers to a composition which allows the application of the agent material to the site of the application, surrounding tissues, or prepared tissue section to allow the agent to have an effective residence time for specific binding to the target or to provide a convenient manner of release. Solubilization strategies may include but are not limited to: pH adjustments, salt formation, formation of ionizable compounds, use of co-solvents, complexation, surfactants and micelles, emulsions and micro-emulsions. The pharmaceutical carrier may include, but is not limited to, a solubilizer, detergent, buffer solution, stabilizers, and preservatives. Examples of these include but are not limited to, HCl, citric acid, DMSO, propylene glycol, ethanol PEG 300, cyclodextrans, citrate, acetate, phosphate, carbonate or tris (hydroxymethyl)aminomethane.

"Demyelination model" refers to any experimentally-induced damage to, or dysfunction of, the insulating material ensheathing portions of neuronal cells, that may be utilized in the experimental study of neuropathic demyelination, including, but not limited to, experimental allergic encephalomyelitis.

"Remyelination" refers to the spontaneous, therapeutic, or experimentally induced repair, regeneration, or otherwise enhanced constitution or functionality of the insulating material ensheathing neuronal axons.

"Alkyl" is intended to include linear, branched, or cyclic hydrocarbon structures and combinations thereof, including lower alkyl and higher alkyl. Alkyl groups are those of C20 or below. "Lower alkyl" refers to alkyl groups of from 1 to 6 carbon atoms, preferably from 1 to 4 carbon atoms, and includes methyl, ethyl, n-propyl, isopropyl, and n-, s- and t-butyl. Higher alkyl refers to alkyl groups having seven or more carbon atoms, preferably 7-20 carbon atoms, and includes n-, s- and t-heptyl, octyl, and dodecyl. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl. Alkenyl and alkynyl refer to alkyl groups wherein two or more hydrogen atoms are replaced by a double or triple bond, respectively.

"Substituted" refers to residues, including, but not limited to, alkyl, alkylaryl, aryl, arylalkyl, and heteroaryl, wherein up to three H atoms of the residue are replaced with lower alkyl, substituted alkyl, aryl, substituted aryl, haloalkyl, alkoxy, carbonyl, carboxy, carboxalkoxy, carboxamido, acyloxy, amidino, nitro, halo, hydroxy, $OCH(COOH)_2$, cyano, primary amino, secondary amino, acylamino, alkylthio, sulfoxide, sulfone, phenyl, benzyl, phenoxy, benzyloxy, heteroaryl, or heteroaryloxy.

"Electron donating group" refers to chemical groups that add electron density to the conjugated $\pi$ system making it more nucleophilic. Electron donating groups may be recognized by lone pairs of electrons on an atom adjacent to the $\pi$ system. Examples of electron donating groups include, but are not limited to, —NR'R", —NHR, —NH$_2$, —NC(NH$_2$)$_2$, —OH, —OR, —SR, —NHCOR, —OCOR, —C$_6$H$_5$, and —CH=CR$_2$.

"Electron withdrawing group" refers to chemical groups that remove electron density from the conjugated $\pi$ system rendering the structure less nucleophilic. Electron withdrawing groups may be recognized either by the atom adjacent to the $\pi$ system having several bonds to more electronegative atoms or, having a formal positive charge. Examples of electron withdrawing groups include, but are not limited to, —CHO, —COR, —COOR, —COOH, —CONH$_2$, —CONHR, —CONR$_2$, —CF$_3$, —CN, C=C(CN)$_2$—SO$_3$H, —NH$_3$+, —NR$_3$+, —NO$_2$, —SOR, —SO$_2$R, —SO$_2$NH$_2$, —SO$_2$NHR, and —SO$_2$NR$_2$.

An agent exhibits "specific uptake" for myelinated tissues if it associates more frequently with, more rapidly with, for a longer duration with, or with greater affinity to, or if it is absorbed more, or accumulates more in myelinated tissues than with non-myelinated tissues. Generally, specific uptake is characterized by a relatively high affinity of an agent to a target.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Many of the compounds described herein may comprise one or more asymmetric centers and may thus give rise to enantiomers, diastereomers, and other stereoisomeric forms that may be defined, in terms of absolute stereochemistry, as (R)- or (S)-. The chemical structure of the agent includes for example, without limitation, all such possible isomers, as well as, their racemic and optically pure forms. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also included.

In certain embodiments, methods for the qualitative or quantitative detection of myelin basic protein in an in vitro or in vivo sample utilizing specific binding of an agent to myelin basic protein is provided. The specific binding to myelin basic protein may be by an a compound of Formula I or its salt

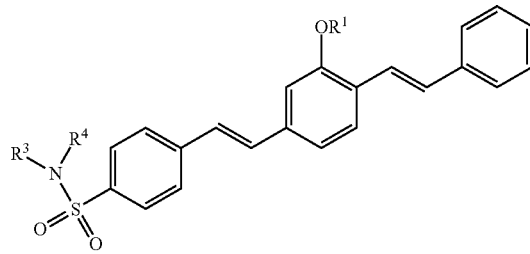

wherein $R^1$ is an alkyl group, $R^2$ is an electron donating group and $R^3$ and $R^4$ are independently hydrogen, alkyl, substituted alkyl, amine, substituted amine, or taken together form a heterocyclic ring or substituted heterocyclic ring structure.

In certain embodiments $R^1$ be a lower alkyl groups of from 1 to 6 carbon atoms, preferably from 1 to 4 carbon atoms, and includes methyl, ethyl, n-propyl, isopropyl, and n-, s- and t-butyl. The electron-donating group, $R^2$, may include a primary, secondary, or tertiary amine, or an alkoxy group. Preferably $R^2$ may be an amine, and more preferably $NH_2$.

In certain embodiments $R^3$ and $R^4$ may be used to improve aqueous solubility and reduce log P of the agent. $R^3$ and $R^4$ may be independently a hydrogen atom or an alkyl, preferably a lower alkyl group of from 1 to 6 carbon atoms. In other embodiments, $R^3$ and $R^4$ may independently be a substituted alkyl groups, such as, but not limited to an alkoxy or alcohol. In certain embodiments, the alkoxy group may contain ethylene glycol units or an ethylene glycol terminated alcohol; for example $(CH_2CH_2O)_nX$ or $CH_2CH_2CH_2(OCH_2CH_2)_nOX$ where n is an integer between 1 and 6 and X is hydrogen, methyl or ethyl. In still other embodiments, when $R^3$ and $R^4$ form an unsubstituted or substituted heterocyclic ring structure. The heterocyclic ring structure may be piperidine, piperazine, or morpholine or an alkyl or alkoxyl substituted piperidine, piperazine, or morpholine.

In each embodiment, $R^2$ and the sulfonamide group $R^3R^4NSO_2$ are conjugated through the π double bond orbitals of the benzene rings and olefinic substituents, thereby providing a clear path for electrons to flow from the electron-donating group to the electron-withdrawing group.

In certain embodiments, the agent may be a salt of Formula I, wherein $R^3$ and $R^4$ may comprise an ammonium cation with an anion. The ammonium salt may be a tertiary ammonium salt wherein the anion may be a halide. In other embodiments the anion may be polyatomic such as, but not limited to a peroxide, carbonate, sulfate, and phosphate. The polyatomic anion may also comprise a halide such as, but limited to, a chlorate, perchlorate, iodate, periodate, bromate, or a combination thereof. In still other examples the anion may be basic active compounds, such as, but not limited to, citrate, tartrate, maleate, malate, fumarate, itaconate, or ascorbate. For in vivo applications, those anions will low biological toxicity would be preferred.

Some non-limiting examples of Formula I, are shown as structures (1)-(3).

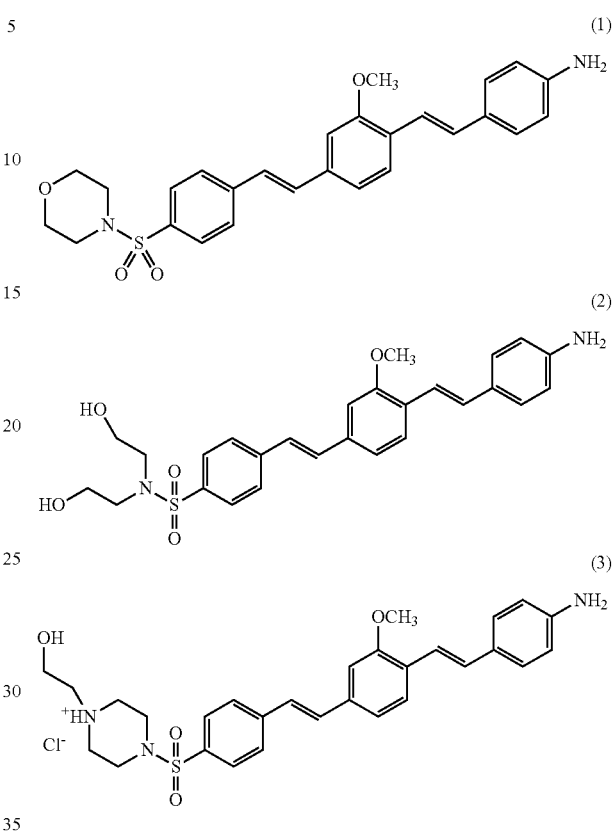

Increase in solubility is obtained in comparison to similar materials such as structures (4) and (5).

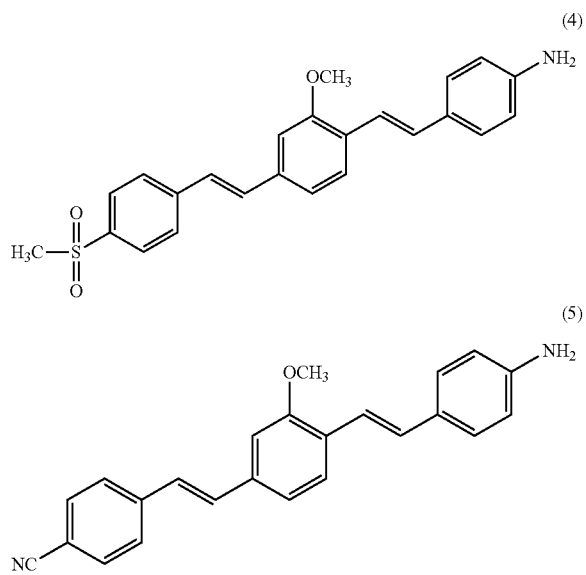

In certain embodiments, agents, which have improved aqueous solubility compared to similar agents, may lessen nonspecific partitioning of the agents to the non-target tissue, such as adipose tissue. Also, improved aqueous solubility may enable the agents to be formulated in pharmaceutical carriers with less or no known toxic effects, thus making them more suitable for use in higher dosage and providing researchers and clinicians important diagnostic and treatment tools.

Figure 2:
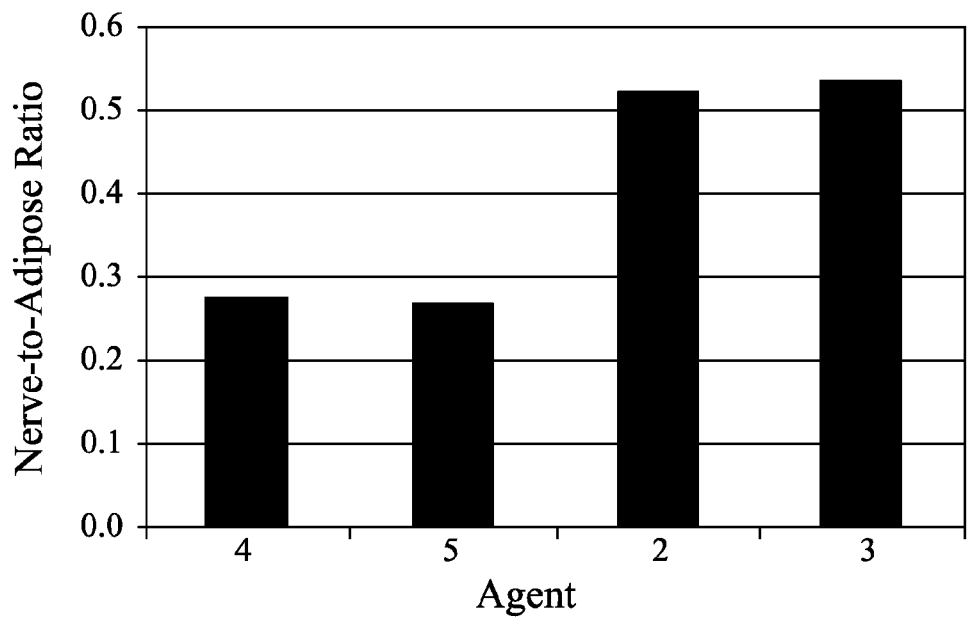
FIG. 2 is a graphical representation of the nerve-to-adipose tissue ratio of agents (2)-(5) at fluorescence emission of 600 nm.
Figure 3:
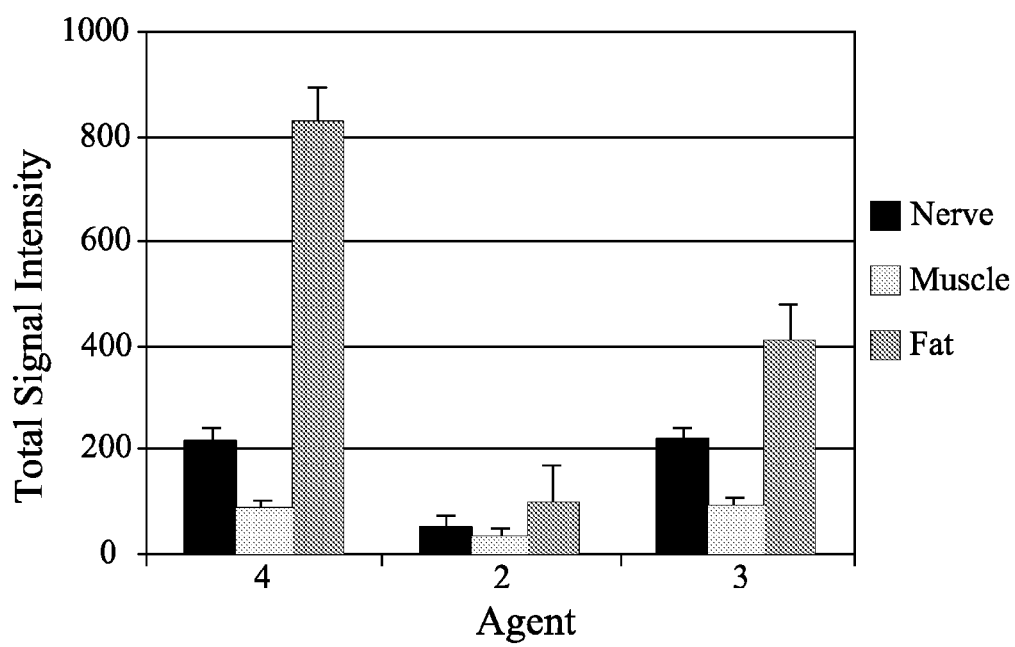
FIG. 3 is a graphical representation of the nerve, muscle and adipose tissue fluorescence emission signal intensity at 600 nm of sulfonamide agents (2) and (3) compared to (4).

Improvement in nerve-to-adipose tissue fluorescence emission intensity is shown in FIG. 2. FIG. 2 is a graphical representation of the nerve-to-adipose tissue ratio of agents (2)-(5) at emission of 600 nm. As shown the sulfonamide agents 2 and 3 maintain a higher nerve-to-adipose tissue ratio compared to agents (4) and (5). FIG. 3 also shows the improvement. FIG. 3 is a graphical representation of the nerve, muscle and adipose tissue fluorescence emission intensity at 600 nm of sulfonamide agents (2) and (3) compared to (4). The reduction in the adipose tissue fluorescence intensity relative to the agents' fluorescence intensity in nerve tissue is apparent. Also shown is each agent's fluorescence intensity in muscle. The ratio of nerve-to-muscle fluorescence intensity is above an experimentally determined cut-off value of 1.3. The cut-off value of 1.3 is a value wherein the nerve and muscle may be readily distinguished.

Figure 4:
FIG. 4 is a graphical representation of nerve-to-muscle ratio of agents (3) and (5) at different time points post-injection of the agents to mice.
Figure 4:
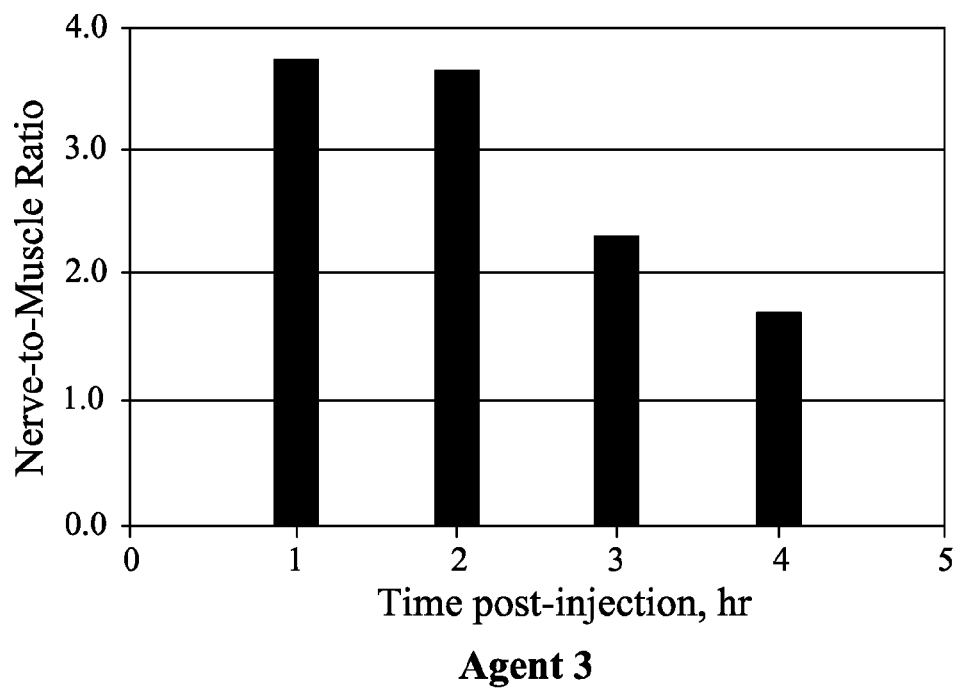

Improvement in the pharmacokinetics over time is shown in FIG. 4. The nerve-to-muscle ratio of agent (3) appears to peak much earlier than agent (5). The nerve-to-muscle ratio of (3) is best at one hour post-injection in mice, compared with agent (5), which is four hours post-injection.

Formula I, or its salt may be detected through its fluorescence signal or optical properties. In some embodiments, the agent may be a radioisotope derivative of Formula I or its salt, including $^{18}$F-labeled derivatives and $^{123}$I-labeled derivatives. In such cases the agent comprising the radioisotope may be detected by its emitted radiation. In other embodiments, Formula I or its salt may be a $^{19}$F-labeled derivative and detected by its emitted signal using magnetic resonance.

As such the method of detection of the labeled agent may include fluorescence microscopy, laser-confocal microscopy, cross-polarization microscopy, nuclear scintigraphy, positron emission tomography ("PET"), single photon emission computed tomography ("SPECT"), magnetic resonance imaging ("MRI"), magnetic resonance spectroscopy ("MRS"), or a combination thereof, depending on the intended use and the imaging methodology available to the medical or research personnel.

For example, in certain embodiments, the $R^3$ or $R^4$ of Formula I may be a fluoroalkyl such as —$CF_3$, —$CH_2CF_3$, or —$OC(CF_3)_3$ for the purpose of MRI imaging. In other examples $R^3$ or $R^4$ may be, —$(CH_2CH_2O)_nQ$ or $CH_2CH_2CH_2O(CH_2CH_2O)_mQ$ where n is an integer between 1 and 5, m is an integer between 0 and 4, and Q is $CH_2CF_3$, $CH(CF_3)_2$, or $C(CF_3)_3$. $R^3$ and $R^4$ also form a ring structure such as fluoroalkyl or fluoroalkoxyl substituted piperidine, piperazine, or morpholine.

For imaging methods using PET imaging, $^{18}$F radioisotopes may be incorporated into Formula I, or its salt, through its $R^1$, $R^2$, $R^3$, or $R^4$ substituents or directly through one of its aromatic rings. For imaging methods using SPECT imaging, $^{123}$I-labeled derivatives may be used. Non-limiting examples of exemplary agents are shown in Table 1.

TABLE 1

Exemplary radioisotopes of Formula I

Isotope
Location $R^1$ $R^1$ $n = 1-4$
$m = 0-2$

US 8,658,129 B2
TABLE 1-continued
Exemplary radioisotopes of Formula I
Isotope
Location
$R^3, R^4$
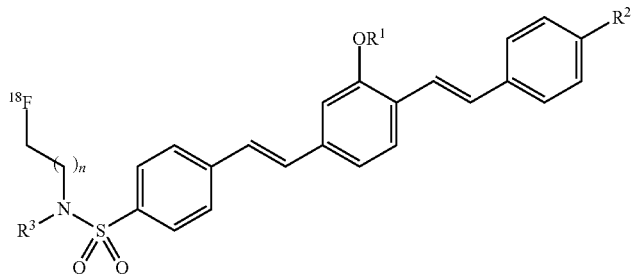
$n = 1-3$
$R^3, R^4$
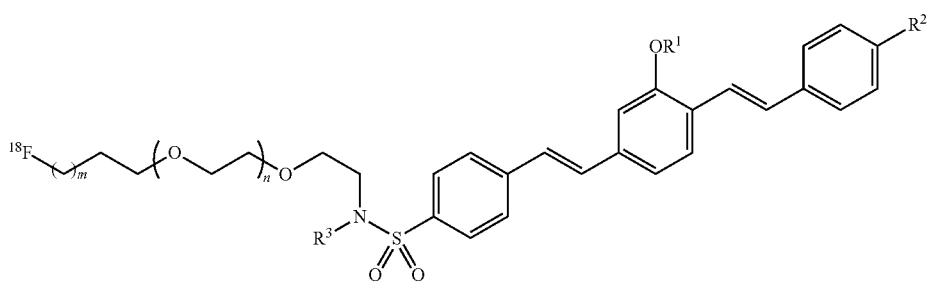
$n = 1-4$
$m = 0-2$
$R^3, R^4$
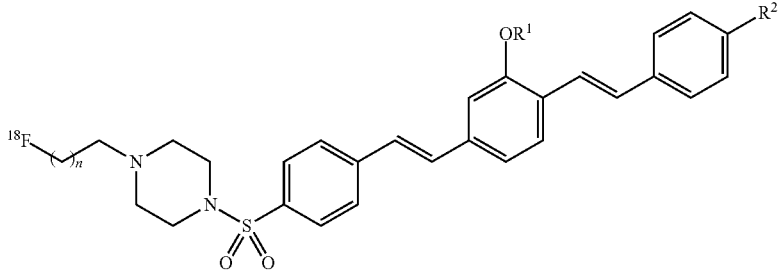
$n = 1-3$
$R^3, R^4$
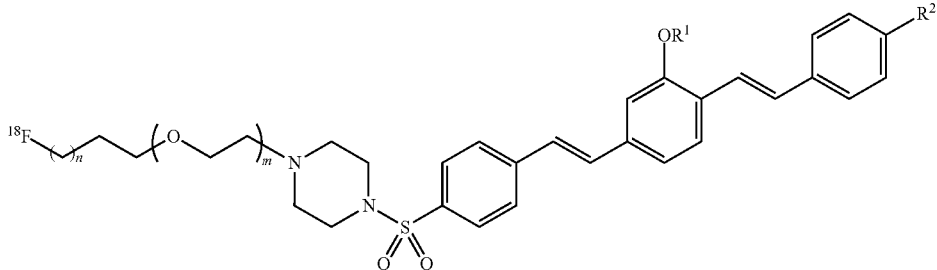
$n = 1-4$
$m = 0-2$ TABLE 1-continued
Exemplary radioisotopes of Formula I
Isotope
Location
R²
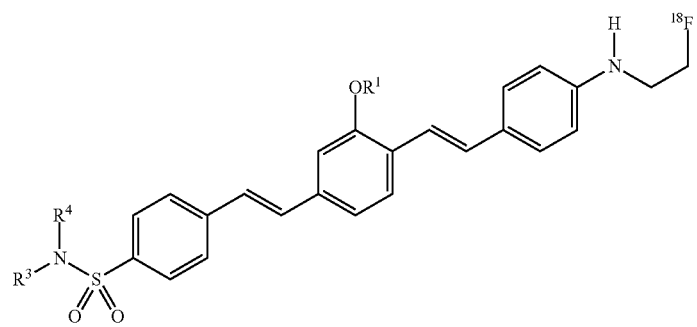
R²
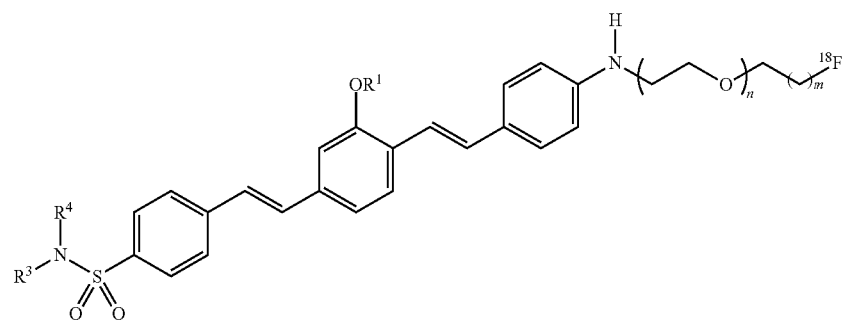
$n = 1\text{-}4$
$m = 0\text{-}2$
Ring
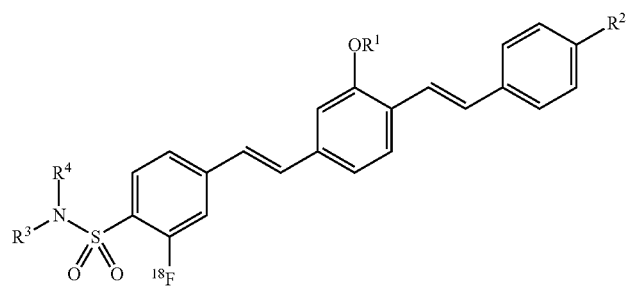
Ring
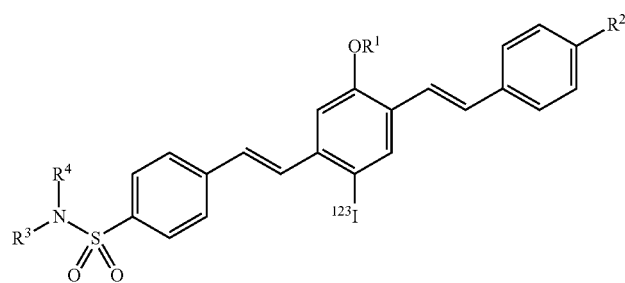

TABLE 1-continued

Exemplary radioisotopes of Formula I

Isotope
Location

Ring

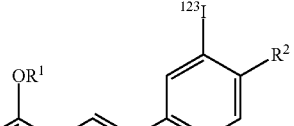

Ring

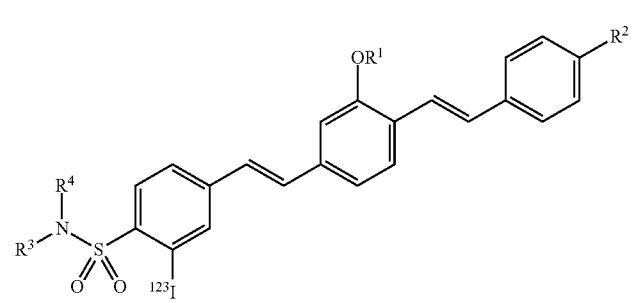

The imaging methods described may be applicable to analytical, diagnostic, or prognostic applications related to myelin basic protein detection. The applications may be particularly applicable in intraoperative nerve labeling, spinal imaging, brain tissue imaging, non-invasive in vivo measurement of myelination levels, and preclinical and basic neuroscience bench research aimed at the study of the function and process of myelination, and the dysfunction and repair of myelin.

In one embodiment, an agent which binds specifically to myelin basic protein may be administered parenterally to a surgical subject prior to surgery such that the agent binds to myelin basic protein and may be cleared from tissues that do not contain myelin basic protein. When used, the term surgery may refer to open surgery or minimally invasive surgery. In another embodiment, the agent may be applied directly, via painting on, spraying on, or local injection to the surgical field during surgery, allowed to bind to myelin basic protein present, and the surgical site washed by lavage to clear unbound composition from the site. During surgery, a light source tuned to the spectral excitation characteristics of the agent may be applied to the surgical field. The agent may be observed through an optical filter tuned to its spectral emission characteristics. Due to their specific binding to the fluorescing agent, nerves and other myelin containing tissue are distinguishable from tissue not containing myelin basic protein. This enables the surgeon to avoid inadvertently cutting or damaging myelinated tissue by avoiding fluorescing tissue, or facilitates accurately administering treatment to the intended myelinated tissue. In certain embodiments the agent comprises the compound of Formula I.

An agent which specifically binds to myelin basic protein may be administered parenterally to a subject prior to surgery or prior to treatments targeting a nerve or other myelin containing tissue, such as pharmaceutical or surgical nerve block.

In certain embodiments the myelinated tissue may be part of the spinal canal and intervertebral foramen. In other embodiments the myelinated tissue may be part of the brain. In certain embodiments the agent comprises a compound of Formula I or its salt. The agent may also be a radioisotope or $^{19}$F-labeled derivative.

In one embodiment the aforementioned agent, may be administered parenterally to a surgical subject, prior to surgery, to permit binding to myelin basic protein, and clearance from tissues that do not contain myelin basic protein without the elimination of specific myelin basic protein binding.

In another embodiment, an agent, which is a radioisotope and which specifically, binds to myelin basic protein may be administered parenterally to a subject prior to treatment to allow binding and clearance from tissues that do not contain myelin. Imaging techniques such as nuclear scintigraphy, PET, SPECT, PET-CT, SPECT-CT, MRI, MRS, or any combination thereof, may then be used to aid in differentiation of the myelin and non-myelin containing tissues and may employ a gamma camera, a scanner or a probe. The agent may be a radioisotope derivative of the compound of Formula I or its salt.

In another embodiment an agent, such as one comprising the compound of a radioisotope derivative of the compound of Formula I or its salt, may be administered parenterally to a patient suspected of, or determined to be, suffering from a spinal pathology, such as but not limited to, spinal compression, spinal nerve root compression, or a bulging disc. After binding to spinal myelin basic protein, and clearance from tissue that does not contain myelin basic protein without eliminating the specific myelin basic protein binding, the spine may be imaged for in vivo using radioisotope imaging such as PET, SPECT, or any combination thereof.

By inspection of the diagnostic images, the clinician may determine if, and where, the spinal cord, or associated nerve roots, are impinged, such as by the vertebral column or foreign matter. Additional scans, such as CT or MRI, may also be conducted in conjunction with PET or SPECT scans, to provide additional information, such as the structure and relative positioning of elements of the vertebral column. In one embodiment, this method may be applied to a surgical procedure to image the spinal region intraoperatively.

In another embodiment, myelination level is accessed in vivo by imaging a radioisotope derivative of the compound of Formula I or its salt. The agent is administered parenterally to a subject diagnosed with, or suspected of having, a myelin-associated neuropathy. After binding to myelin basic protein, and clearance from tissue that does not contain myelin basic protein without eliminating specific myelin basic protein binding, components of the central or peripheral nervous system may be imaged by a method suitable for in vivo imaging of the radioisotope. Such methods include PET and SPECT. By inspection of the imaging results, the clinician may determine the amount of myelination, as reflected by levels and anatomical localization of signal emitted by the radioisotope derivative of the agent and detected by the appropriate imaging methodology.

To determine whether myelination in the patient may be deficient, myelination levels may be compared to those exhibited by a subject or subjects believed or known not to be suffering from a myelin-associated neuropathy. In another embodiment, rates of demyelination or remyelination may be determined. Following treatment with a known or suggested therapeutic agent believed or anticipated to prevent or slow demyelination or to promote remyelination in patients suffering from myelin-associated neuropathies, myelination levels are evaluated by performing the imaging over time in the patients treated with the therapeutic agent. The imaging may be performed at different points of time and the level of myelination at one time point compared to that of another. As such level of myelination may be determined qualitatively or quantitatively.

A positive result suggestive of a myelin-associated neuropathy may be one in which the decrease of myelin basic protein of the subject, compared to a baseline measurement of myelin basic protein, in a control sample is statistically significant. The control sample may be from a similar sample free of a myelin-associated neuropathy or from the same subject with measurements taken over time.

In yet another embodiment, a biopsied mammalian tissue sample, or a tissue sample cultured in vitro, may be contacted with an agent specific for binding to myelin basic protein. The agent may comprise a compound of Formula I or its salt. The agent may also be a radioisotope or $^{19}$F-labeled derivative of Formula I or its salt. Contacting with the agent may be used to determine the location, presence, or amount of myelin basic protein in the tissue sample. The tissue sample may be sampled from a subject that has been experimentally manipulated so as to serve as a verified or purported model of myelin-associated neuropathy, or that has received at least one therapeutic agent verified as, or purported to be, a treatment for myelin-associated neuropathy. The therapeutic agent may be associated with the preclinical evaluation or basic neuroscience research aimed at studying the function and process of myelination, and the dysfunction and repair of myelin.

Fresh frozen cryostatic sections, or fixed or embedded sections or samples, of the biopsy or culture tissue sections, may be contacted with an agent specific for binding to myelin basic protein. The samples may be prepared using various sectioning techniques such as microtome, vibratome, or cryostat preparation. The agent may a compound of Formula I or its salt. The agent may also be a radioisotope or $^{19}$F-labeled derivative of Formula I or its salt.

After binding to myelin basic protein, the sample may be washed in a manner and medium suitable to remove any unbound and non-specifically bound label from the sample, without eliminating specific binding to myelin basic protein.

In certain embodiments, a pharmaceutical carrier may be used to enhance solubility or bioavailability of an agent comprising a compound of Formula I or its salt, a radioisotope or $^{19}$F-labeled derivative of Formula I or its salt. in the various aforementioned administration methods. Water-soluble organic solvents may be used such as, but not limited to, polyethylene glycol 400 (PEG 400), ethanol, propylene glycol, and glycerin. Water-insoluble organic solvents may also be used alone or as a cosolvent or for solubilization. Other pharmaceutical carriers may include, but are not limited to, surfactants including non-ionic surfactants, lipids including triglycerides, cyclodextrins, and phospholipids as well as other detergents, buffer solutions, stabilizers, and preservatives. In each case the use of both water-soluble and water-insoluble organic solvents may be used in combination with other pharmaceutical carriers to limit the occurrence of precipitation, pain, inflammation and homolysis upon administration. For example, in certain embodiments the pharmaceutical carrier may comprise 5 to 20% (volume/volume) propylene glycol, 5 to 30% (weight to volume) 2-hydroxylpropyl-β-cyclodextrin, and 70 to 90% distilled deionized water (volume to volume).

Techniques to enhance solubility of the agent may include, pH adjustment, cosolvents, complexation, emulsions, micelles, and liposomes. The pharmaceutical carrier may also include, but is not limited to, surfactants such as a detergent, buffer solutions, stabilizers, and preservatives.

In certain embodiments, an agent comprising, a compound of Formula I or its salt, or a radioisotope or $^{19}$F-labeled derivative of Formula I or its salt, may be packaged and provide in the form of a kit that ensures sterility of the agent is maintain as well as other critical parameters such as pH, solubility, and concentration. The kit would comprise the agent in, in a form suitable for administration such as dissolved in a pharmaceutical carrier.

In certain embodiments the agent may be stored separate from the pharmaceutical carrier. As such, a kit may comprise a multi-chamber configuration, such as a pre-loaded dual chamber syringe or vial, or separate vials containing selected quantities of agents and carrier. Such syringes and vials may maintain separation between the agent and one or more pharmaceutical carrier, but permit mixing prior to administration. In certain embodiments, the kit may be configured such that one chamber may contain a pharmaceutical carrier and the agent, and additional chambers comprise other solvents or agents wherein separate storage allows for longer shelf-life or to maintain the efficacy of the agent. Still other embodiments may provide features to allow changes to concentration or to alter the composition of the pharmaceutical carrier or to enhance activity of the agent.

Any of a number of detection, visualization, or quantitation techniques, including but not limited to fluorescence microscopy, laser-confocal microscopy, cross-polarization microscopy, autoradiography, MRI, MRS, or other applicable methods, or any combination thereof, may be then be used to assess the presence or quantity of an agent having specific binding to myelin basic protein in the tissue sample and may represent the presence or amount of myelin basic protein. In certain embodiments, the agent may comprise a compound of Formula I or its salt. The agent may also be a radioisotope or $^{19}$F-labeled derivative of Formula I or its salt. The labeling with, and detection, visualization, or quantitation of the an agent, may also be performed in conjunction with labeling with, and detection, visualization, or quantitation of at least one other compound that specifically binds a substance other than myelin basic protein.

absorbance is recorded and used as the excitation wavelength for future fluorescence measurements.

The fluorescence spectra of the agents were collected in DMSO, MeOH, and ddH$_2$O under continuous excitation using a xenon short arc light source (Ushio UXL 75W, Ushio America, Inc., Cyress Calif.) equipped fluorimeter (350-900 nm; PTI Fluorimeter, Photon Technology International Birmingham, N.J.). A summary of the excitation maxima and fluorescence emission maxima findings is shown in Table 2. A+ indicates binding to nerves using the ex vivo histochemical assay.

TABLE 2

Optical Characterization of Sulfonamide Agents

| Structure | Nerve binding, ex vivo | Excitation (DMSO) | Emission(DMSO) | Excitation(MeOH) | Emission(MeOH) | ExcitationddH2O | EmissionddH2O |
| --- | --- | --- | --- | --- | --- | --- | --- |
| (1) | + | 422 | 621 | 392 | 604 | 380 | 581 |
| (2) | + | 392 | 600 | 391 | 680 | 409 | 620 |
| (3) | + | 388 | 615 | 380 | 488 | 412 | 626 |

EXAMPLES

The following non-limiting Examples are shown and describe various embodiments of the present invention.

Preparation of Nerve Tissue Sections

Various nerves including sciatic, femoral, brachial plexus, trigeminal, optic, and penile were harvested from male Sprague Dawley rats or male CD-1 mice. Tissue was fixed by perfusion and/or post-fixation with formalin. Following post-fixation, tissue was cryoprotected in a 20% sucrose solution made in phosphate buffered saline (PBS). Nerves were then flash-frozen using methanol and dry ice in OCT media. In some cases, PVDF membranes were used to help keep the nerves vertical in the OCT media. Thin sections (5-10 microns) were sliced on a Leica microtome (Leica Microsystems GmbH, Wetzlar Germany) and stored in a −80° C. freezer prior to staining with agents (1)-(5).

Ex Vivo Staining of Nerve Tissue Sections by the Agents

The agents were dissolved in DMSO to make a 10 mM stock solution. Slides containing nerve tissue sections were rinsed three times with PBS. The tissue sections were incubated with a solution of 10 uM of each fluorophore diluted in either PBS or a mixture of 99 uL DMSO, 100 uL cremaphor, 600 uL rat serum, and 200 uL PBS for 20 minutes. The slides were then washed with PBS for 5 min three times, cover-slipped with Vectashield and imaged on a Zeiss Axioimager microscope (Carl Zeiss Meditec, Inc., Oberkochen, Germany) at 200× magnification. A custom filter cube (excitation filter: 387 nm with 11 nm bandpass, 409 nm dichroic mirror; emission filter 409 nm long pass) was used to collect images for examination of morphology and for image analysis.

FIG. 1 shows staining of the trigeminal nerves with agents (1), (2), and (3). As shown, the myelinated donut-shaped structures are visible. The control slides, containing the nerves with no agent (not shown), was negative under the same imaging conditions.

In Vitro Characterization of Sulfonamide Agents

Absorbance spectra of the agents were measured using a UV-Vis spectrometer (PerkinElmer Lambda™ 20, PerkinElmer, Inc., Waltham Mass.) in wavelengths ranging from 200-to-800 nm in 100% dimethylsulfoxide (DMSO), absolute methanol (MeOH), and distilled/deionized water (ddH$_2$O). The wavelength corresponding to the maximum Log P and Solubility Aqueous solubility and log P were calculated using the Accelrys Discovery Studio® software (Accelrys Inc., San Diego, Calif.). The aqueous solubility model uses linear regression to predict the solubility of the compounds in water at 25° C. Values that are close to −8 are predicted to have low aqueous solubility, and values close to 0 are more soluble. Log P is the logarithm of octanol-water partition coefficient, and is a measure of lipophilicity. The nerve-labeling agents are lipophilic to enable them to penetrate the tight junctions of the blood brain barrier and blood nerve barrier. The optimal log P for blood brain barrier penetration is between 1-4, with higher log P associated with increased non-specific partitioning in adipose tissue. Table 3 shows a summary of the solubility and log P calculations.

TABLE 3

Calculated aqueous solubility and logP

| Structure | Solubility | logP |
| --- | --- | --- |
| (1) | −4.82 | 3.8 |
| (2) | −3.27 | 3.1 |
| (3) | −4.04 | 3.7 |
| (4) | −5.35 | 4.6 |
| (5) | −5.42 | 4.9 |

Dynamic light scattering spectroscopy was used to measure aqueous solubility. Measurements were collected on a Malvern HPPS500 spectrometer (Malvern Instruments Inc., Southborough, Mass.). Samples were measured in a low volume disposable cuvette at 25° C., at an angle of 173°. Each sample was analyzed in duplicate. Z average measurements were taken to determine the relative molecular "size" of the formulation in terms of the hydrodynamic diameter (DH) radius in solution. DH is inversely related the z-average translational diffusion coefficient (D) in the solution. Table 4 shows a summary for compound sulfonamide compound (3) and non-sulfonamide compounds (4) and (5).

TABLE 4

Dynamic light scattering measurements for aqueous solubility ranking

| Structure | Z-average | Rank in solubility |
|---|---|---|
| (3) | 29.70 | 1 |
| (4) | 2210.00 | 2 |
| (5) | 7365.00 | 3 |

Formulation, Dosing, and Kinetics for In Vivo Fluorescence Imaging:

To assess the efficacy of the sulfonamide agents in-vivo the agents were formulated using the following excipients: 5-20% propylene glycol (v/v; JT Baker 9402-01), 5-30% 2-Hydroxylpropyl-β-Cyclodextrin (w/v; Sigma H5784) and 70-90% distilled/deionized water (v/v).

To prepare the pharmaceutical carrier, each excipient is added individually beginning with propylene glycol. Propylene glycol is added directly to the agent and vortexed for approximately 1 minute to guarantee maximal dispersal of the agent in the excipient. The next excipient to be added to the solution is 2-Hydroxylpropyl-β-Cyclodextrin. Cyclodextrin's are cyclic (R-1,4) linked oligosaccharides containing a relatively hydrophobic central cavity and hydrophilic outer surface. The application of cyclodextrin in formulation is to enhance the solubility of a compound in aqueous solutions. In formulation of the sulfonamide analogs a final concentration of 5-15%; 2-Hydroxypropyl β-cyclodextrin (w/v) is added to the solution. The formulation is again vortexed for 1-5 minutes and the pH adjusted to a final range between 4-5. The final step in the formulation is to bring the solution to the volume with distilled/deionized water.

In-Vivo Fluorescence Imaging:

Male CD-1 mice between 25-35 grams were purchased from Charles River Laboratories (Wilmington, Mass.). Prior to administration of the agent, animals were briefly anesthetized using 2% isofluorane. Each agent was then administered in a 15.2 mg/kg dose via tail vein catheterization. Each rodent was allowed to recover from anesthesia prior to returning to the home cage.

Structure (2) and (3) were administered at an average of 15 mg/kg formulated in the pharmaceutical carrier. Formulated agents were administered in mice 4 hours prior to imaging using a Zeiss Lumara microscope (Carl Zeiss Meditec, Inc., Oberkochen, Germany) with an attached CRI Nuance™ camera for multispectral fluorescence imaging (Cambridge Research & Instrumentation, Inc., Woburn, Mass.). The excitation wavelengths used were 406/15 nm or 460/60 nm.

Figure 5A:
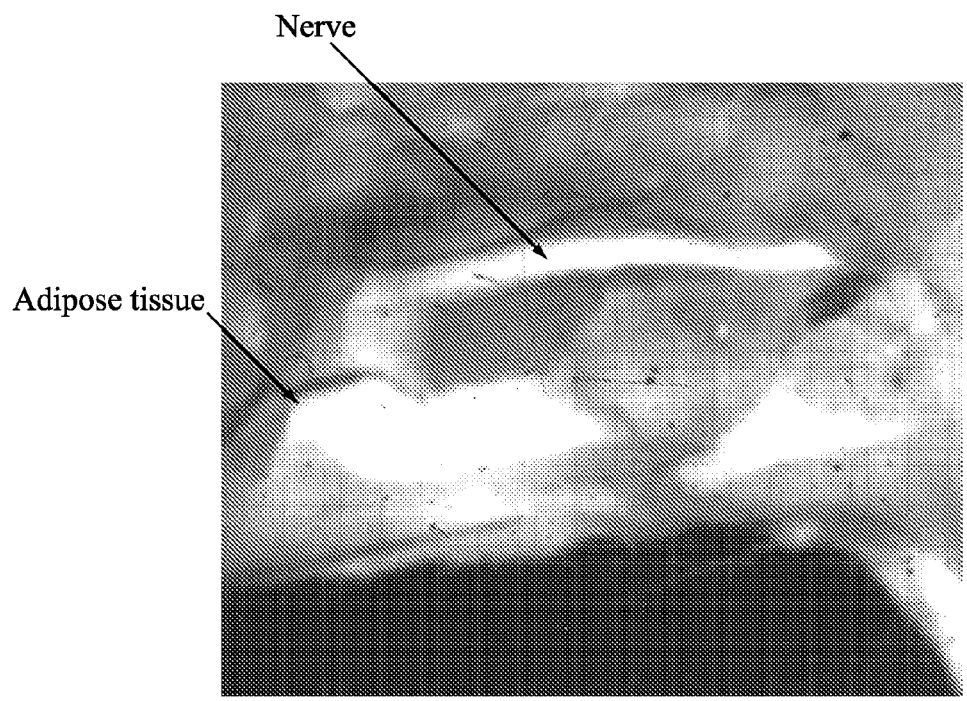
FIG. 5A shows results from fluorescence imaging of an adult mouse sciatic nerve 4 hours post administration of the sulfonamide agent structure (2)
Figure 5B:
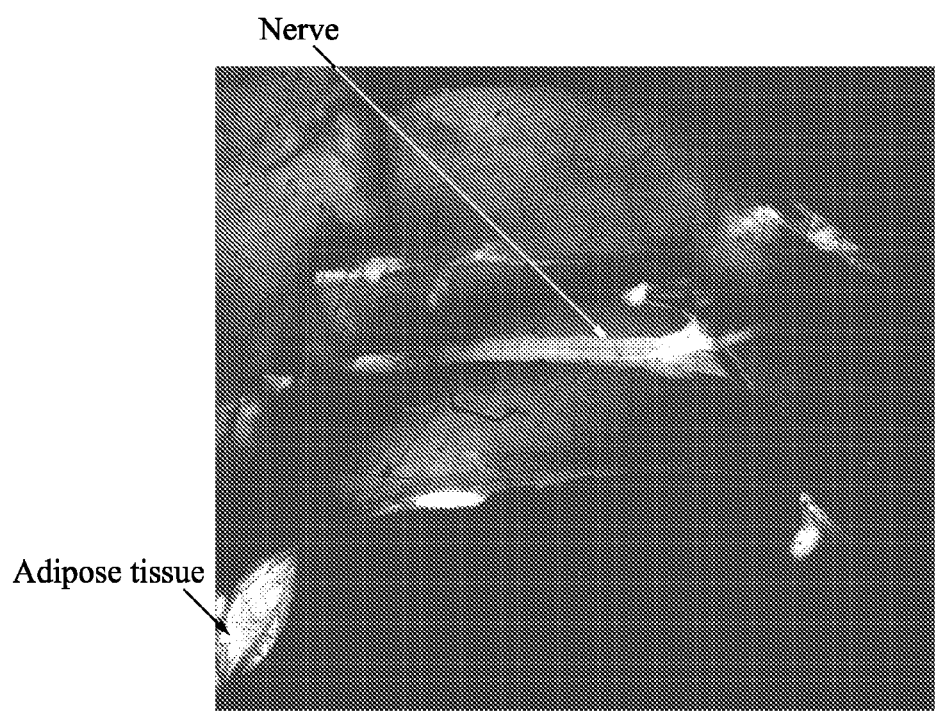
FIG. 5B shows results from fluorescence imaging of a sciatic nerve 4 hours post administration of the sulfonamide agent structure (3).

When the agents were injected systemically to the preclinical animal model, in vivo imaging revealed that the agents localized to nerves in a number of tissues including the brachial plexus, facial nerve, trigeminal nerve, phrenic nerve, vagus nerve and optic nerve. The adjacent muscle tissues had very low background binding. The nerves of the negative control animals, with no agent administered, had no fluorescent signal. FIG. 5A shows results from fluorescence imaging of an adult mouse sciatic nerve 4 hours post administration of the sulfonamide agent structure (2). FIG. 5B shows results from fluorescence imaging of a sciatic nerve 4 hours post administration of the sulfonamide agent structure (3).

Scheme 1: Synthesis of Structure (1);

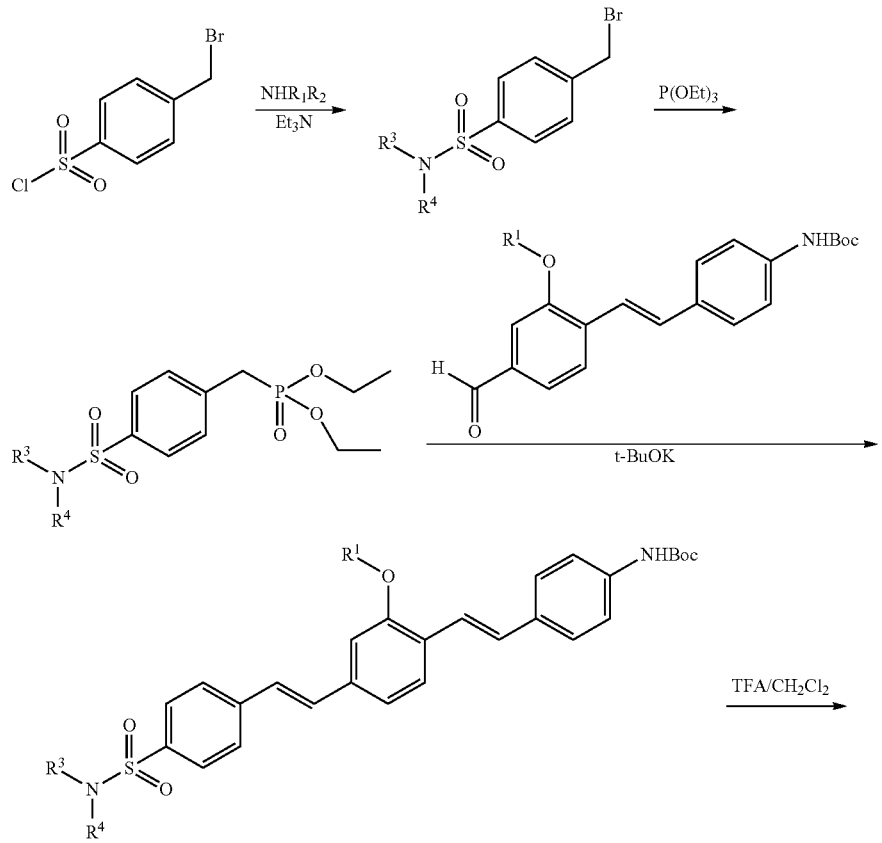

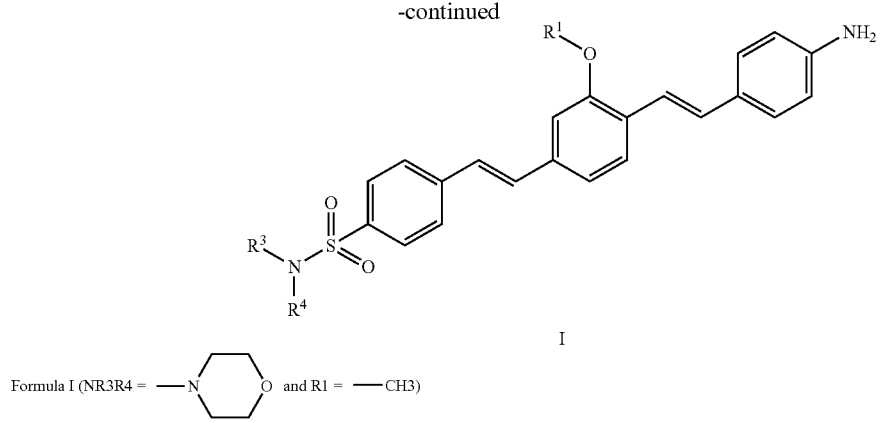

Preparation of the key intermediate (E)-tert-butyl 4-(4-formyl-2-methoxystyryl)phenylcarbamate by Heck-coupling reaction: 4-bromo-3-methoxybenzaldehyde (106 mg, 0.49 mmol), tert-butyl 4-vinylphenylcarbamate (141 mg, 0.64 mmol), palladium acetate (17 mg, 0.074 mmol), 3,3',3"-phosphinidynetris(benzenesulfonic acid) trisodium salt (TPPTS, 70 mg, 0.12 mmol), and potassium carbonate (205 mg, 1.48 mmol) were dissolved in water/DMF (1:1 v/v, 2.5 mL). The reaction was heated at 95° C. for 3 hrs. The solution was diluted with ethyl acetate and the aqueous layer was extracted with ethyl acetate (3×). The combined organic layers were washed with brine, dried over $Na_2SO_4$, and filtered. MPLC purification (0-25% ethyl acetate/hexanes) yielded the desired product as a yellow solid (122 mg, 70% yield). $^1$H NMR (400 MHz, $CD_2Cl_2$) δ ppm: 9.97 (s, 1H), 7.78 (d, J=7.8 Hz, 1H), 7.54 (d, J=8.6 Hz, 2H), 7.50 (d, J=8.0 Hz, 1H), 7.48-7.42 (m, 4H), 7.27 (d, J=16.6 Hz, 1H), 6.77 (s, 1H), 3.99 (s, 3H), 1.55 (s, 9H).

4-(4-(Bromomethyl)phenylsulfonyl)morpholine (compound 1): To a solution of 4-bromomethylbenzenesulfonyl chloride (1.62 g, 6.01 mmol) in anhydrous diethyl ether (10 mL) at −10° C. was added a solution of morpholine (0.52 mL, 5.94 mmol) and triethylamine (0.92 mL, 6.6 mmol) in anhydrous diethyl ether (10 mL). The resulting mixture was allowed to warm up to room temperature over 1 hr, and continue stirring at r.t. overnight. The reaction mixture was then diluted with water, extracted with ethyl acetate (2×30 mL). The combined organic layers were washed with water, brine, dried over $Na_2SO_4$, and filtered. Solvents were removed to yield an orange oil, which was purified on a 40 g silica gel column to give a white solid (1.34 g, 71% yield). $^1$H NMR ($CD_2Cl_2$) δ ppm: 7.75 (d, J=8.4 Hz, 2H), 7.63 (d, J=8.4 Hz, 2H), 4.58 (s, 2H), 3.77-3.73 (m, 2H), 3.03-2.98 (m, 2H). MS (ESI+): 320 (M+H)$^+$.

Diethyl 4-(morpholinosulfonyl)benzylphosphonate (compound 2): The aforementioned compound 1, (500 mg, 1.56 mmol) and triethyl phosphite (1.07 mL, 6.24 mmol) was mixed and heated to 100° C. for 1 hr. The reaction mixture was subjected to $N_2$ flow over weekend to remove the excess ethyl phosphite. The resulting yellow oil was purified on a 12 g silica gel column to yield a colorless oil (420 mg, 71% yield). 1H NMR ($CD_2Cl_2$) δ ppm: 7.72 (d, J=8.4 Hz, 2H), 7.54 (dd, J1=8.4 Hz, J2=2.4 Hz, 2H), 4.1-4.0 (m, 4H), 3.77-3.72 (m, 4H), 3.25 (d, J=22.4 Hz, 2H), 3.02-2.96 (m, 4H), 1.27 (t, J=7.2 Hz, 6H).

tert-Butyl-4-(2-methoxy-4-(4-(morpholino sulfonyl) styryl)styryl)phenylcarbamate (compound 3): To a dry vial containing compound 2 (104.7 mg, 0.28 mmol) under $N_2$ was added dry THF (3 mL) followed by drop-wise addition of a solution of potassium tert-butoxide (35.5 mg, 0.32 mmol) in dry THF (1.5 mL) at 0° C. The ice bath was removed after 20 mins, and a solution of (E)-tert-butyl 4-(4-formyl-2-methoxystyryl)phenylcarbamate (93.4 mg, 0.26 mmol) in dry THF (1.5 mL) was added dropwise. The reaction mixture was heated at 60° C. for 4 hr, at which time the LC/MS showed the reaction was complete. The reaction volume was reduced under a $N_2$ stream, ethyl acetate and brine was added, and the pH of the aqueous layer was adjusted to 3 with dilute (0.1 N) HCl. The mixture was shaken, the layers were separated, and the aqueous layer was extracted with ethyl acetate (2×30 mL). The combined organic layers were dried over $Na_2SO_4$ and filtered. Solvents were removed, and the residue was purified on a 12 g silica gel column to give the desired product 3 (116 mg, 76% yield). $^1$H NMR (CD2Cl2) δ ppm: 7.79-7.71 (m, 4H), 7.64 (d, J=8.0 Hz, 1H), 7.52 (d, J=8.4 Hz, 2H), 7.47-7.40 (m, 1H), 7.42 (d, J=7.2 Hz, 2H), 7.34-7.27 (m, 1H), 7.25-7.18 (m, 3H), 7.15 (d, J=8.4 Hz, 1H), 6.80 (s, 1H), 3.99 (s, 3H), 3.8-3.74 (m, 4H), 3.07-3.01 (m, 4H), 1.56 (s, 9H). MS (ESI+): 577 (M+H)+.

4-(2-Methoxy-4-(4-(morpholinosulfonyl)styryl)styryl) aniline (compound 4): To a solution of compound 3 (70 mg, 0.12 mmol) in $CH_2Cl_2$ was added 20% TFA in $CH_2Cl_2$ (2 mL). The solution was stirred for 2.5 hrs and coated with silica gel. 0.7 mL of triethylamine was added, and the residue was purified on a 12 g silica gel column using dichloromethane (A)-20% methanol/dichloromethane (B), each containing 0.3% triethylamine, with gradient 0-60% B v/v to yield 4 as an orange solid (53 mg, 91% yield). $^1$H NMR (CD2Cl2) δ ppm: 7.78-7.72 (m, 4H), 7.63 (d, J=8.0 Hz, 1H), 7.43 (d, J=8.6 Hz, 1H), 7.39 (d, J=8.4 Hz, 1H), 7.35-7.27 (m, 2H), 7.24-7.17 (m, 2H), 7.15 (d, J=5 Hz, 2H), 7.14-7.10 (m, 1H), 6.80 (d, J=8.6 Hz, 1H), 6.71 (d, J=8.4 Hz, 1H), 3.99 (s, 3H), 3.79-3.74 (m, 4H), 3.06-3.00 (m, 4H). MS (ESI+): 477 (M+H)+.

4-(Bromomethyl)-N,N-bis(2-(tert-butyldimethylsilyloxy) ethyl)benzenesulfonamide (compound 5): To a solution of 4-bromomethylbenzenesulfonyl chloride (2.69 g, 10 mmol) in anhydrous $CH_2Cl_2$ (30 mL) at 0° C. was added Hunig's base (3.39 mL, 20 mmol) followed by drop-wise addition of a solution of bishydroxyethylamine (0.97 g, 9.22 mmol) in anhydrous $CH_2Cl_2$ (3 mL). The reaction was stirred for 6 hrs, after which time more Hunig's base (3.39 mL, 20 mmol) was added, followed by the drop-wise addition of a solution of tert-butyldimethylchlorosilane (2.92 g, 19.4 mmol) in anhydrous $CH_2Cl_2$ (5 mL). The reaction mixture was allowed to slowly warm up to room temperature while being stirred overnight, then washed with water (3×), brine (1×), dried over Na₂SO₄, and filtered. Solvents were removed, and the residue was purified on a 40 g silica gel column to give 5 (2.43 g, 47% yield). ¹H NMR (CD2Cl2) δ ppm: 7.85 (d, J=8.4 Hz, 2H), 7.58 (d, J=8.4 Hz, 2H), 4.68 (s, 2H), 3.76 (t, J=6.2 Hz, 4H), 3.37 (t, J=6.2 Hz, 4H), 0.90 (s, 18H), 0.07 (s, 12H).

Diethyl 4-(N,N-bis(2-(tert-butyldimethylsilyloxy)ethyl) sulfamoyl)benzylphosphonate (compound 6): A 5 mL CEM Pyrex vial containing a magnetic stir bar was charged with compound 5 (566 mg, 1.00 mmol) and 3.0 mL of triethyl phosphite (excess, neat) and sealed with a snap cap. The tube was positioned in the microwave cavity and irradiated for 1.0 hour, at 200 watts, 180° C. (monitored by TLC and LC-MS). After allowing the tube to cool to room temperature, the excess phosphite was evaporated with nitrogen overnight. The resulting residue was purified by flash column chromatography (silica gel column, 0-70% EtOAc in hexanes) yielding 6 as a colorless oil (468 mg, 75% yield). ¹H NMR (CD2Cl2) δ ppm: 7.79 (d, J=8.4 Hz, 2H), 7.48 (dd, J1=8.4 Hz, J2=2.4 Hz, 2H), 4.14-4.00 (m, 4H), 3.77 (t, J=6.2 Hz, 4H), 3.33 (t, J=6.4 Hz, 4H), 3.22 (d, J=22.2 Hz, 2H), 1.34 (t, J=7.2 Hz, 3H), 1.27 (t, J=7.2 Hz, 3H), 0.91 (s, 18H), 0.07 (s, 12H). MS (ESI+): 624 (M+H)+, 646 (M+Na)+.

tert-Butyl 4-(4-(4-(N,N-bis(2-(tert-butyldimethylsilyloxy)ethyl)sulfamoyl)styryl)-2-methoxystyryl)phenylcarbamate (compound 7): To a dry vial containing compound 6 (193 mg, 0.31 mmol) under N₂ was added dry THF (2 mL) followed by drop-wise addition of a solution of potassium tert-butoxide (39 mg, 0.35 mmol) in dry THF (1.5 mL) at 0° C. The ice bath was removed after 20 mins, and a solution of (E)-tert-butyl 4-(4-formyl-2-methoxystyryl)phenylcarbamate (104 mg, 0.29 mmol) in dry THF (1.5 mL) was added dropwise. The reaction mixture was heated at 60° C. overnight. Solvent was removed under a N₂ stream, and the residue was purified on a 12 g silica gel column to give the desired product 7 (114 mg, 48% yield). ¹H NMR (CD2Cl2) δ ppm: 7.84 (d, J=8.4 Hz, 2H), 7.69 (d, J=8.4 Hz, 2H), 7.64 (d, J=8.2 Hz, 1H), 7.52 (d, J=8.6 Hz, 2H), 7.46-7.39 (m, 3H), 7.31-7.19 (m, 4H), 7.17-7.13 (m, 1H), 6.80 (s, 1H), 4.0 (s, 3H), 3.82-3.78 (m, 4H), 3.42-3.35 (m, 4H), 1.56 (s, 9H), 0.92 (s, 18H), 0.09 (s, 12H). MS (ESI+): 845 (M+Na)+.

4-(4-(4-Amino styryl)-3-methoxystyryl)-N,N-bis(2-hydroxyethyl)benzenesulfonamide (compound 8): To a solution of compound 7 (50 mg, 0.06 mmol) in CH₂Cl₂ (0.5 mL) was added 40% TFA in CH₂Cl₂ (0.5 mL). The solution was stirred for 2 hrs and purified on reverse phase high pressure liquid chromatography (RP-HPLC) to give the desired product 8 (17 mg, 57% yield). MS (ESI+): 495 (M+H)+, 517 (M+Na)+.

1-(4-(Bromomethyl)phenylsulfonyl)-4-(2-(tert-butyldimethylsilyloxy)ethyl)piperazine (compound 9): To a solution of 4-bromomethylbenzenesulfonyl chloride (6 g, 22.3 mmol) in anhydrous CH₂Cl₂ (60 mL) at 0° C. was added Hunig's base (15.4 mL, 90.8 mmol) followed by addition of a solution of 1-(2-hydroxyethyl)piperazine (2.5 mL, 20.6 mmol) in anhydrous CH₂Cl₂ (10 mL). The reaction was stirred for 5 hrs, followed by the addition of tert-butyldimethylchlorosilane (3.48 g, 23.2 mmol). The reaction mixture was allowed to slowly warm up to room temperature while being stirred overnight, then washed with water (3×), brine (1×), dried over Na₂SO₄, and filtered. Solvents were removed, and the residue was purified on a 120 g silica gel column to give 9 (5 g, 51% yield). ¹H NMR (CD₂Cl₂) δ ppm: 7.77 (d, J=8.4 Hz, 2H), 7.62 (d, J=8.4 Hz, 2H), 4.69 (s, 2H), 3.68 (t, J=6.0 Hz, 2H), 3.04-3.00 (m, 4H), 2.63-2.59 (m, 4H), 2.51 (t, J=6.0 Hz, 2H), 0.89 (s, 9H), 0.04 (s, 6H).

Diethyl 4-(4-(2-(tert-butyldimethylsilyloxy)ethyl)piperazin-1-ylsulfonyl)benzylphosphonate (compound 10): Compound 9 (590 mg, 1.24 mmol) and triethyl phosphite (1.69 mL, 9.88 mmol) was mixed and heated to 100° C. for 78 hrs, at which time LC/MS showed the reaction was complete. The reaction mixture was subjected to N₂ flow over weekend to remove the excess ethyl phosphite. The resulting residue was purified on a 12 g silica gel column to yield 10 (352 mg, 53% yield). ¹H NMR (CD₂Cl₂) δ ppm: 7.71 (d, J=8.4 Hz, 2H), 7.52 (dd, J1=8.4 Hz, J2=2.4 Hz, 2H), 4.16-4.00 (m, 4H), 3.68 (t, J=6.0 Hz, 2H), 3.24 (d, J=22.0 Hz, 2H), 3.07-2.98 (m, 4H), 2.63-2.58 (m, 4H), 2.50 (t, J=6.0 Hz, 2H), 1.27 (t, J=7.2 Hz, 6H), 0.89 (s, 9H), 0.04 (s, 6H). MS (ESI+): 536 (M+H)+.

tert-Butyl 4-(4-(4-(2-(tert-butyldimethylsilyloxy)ethyl) piperazin-1-ylsulfonyl)styryl)-2-methoxystyryl)phenylcarbamate (compound 11): To a dry vial containing compound 10 (176 mg, 0.31 mmol) under N₂ was added dry THF (2 mL) followed by drop-wise addition of a solution of potassium tert-butoxide (42 mg, 0.38 mmol) in dry THF (1.5 mL) at 0° C. The ice bath was removed after 1.5 hrs, and the reaction mixture was allowed to stir at room temperature for another 25 mins before being subjected to the dropwise addition of a solution of (E)-tert-butyl 4-(4-formyl-2-methoxystyryl)phenylcarbamate (111 mg, 0.31 mmol) in dry THF (1.5 mL) at 0° C. followed by heating at 60° C. overnight. The reaction mixture was purified on a 12 g silica gel column to yield the desired product 11 (118 mg, 51% yield). 1H NMR (CD2Cl2) δ ppm: 7.80-7.70 (m, 4H), 7.64 (d, J=8.0 Hz, 1H), 7.52 (d, J=8.6 Hz, 2H), 7.47-7.39 (m, 3H), 7.33-7.12 (m, 5H), 6.86 (s, 1H), 3.99 (s, 3H), 3.72 (t, J=5.8 Hz, 2H), 3.20-3.00 (m, 4H), 2.75-2.64 (m, 4H), 2.55 (t, J=5.8 Hz, 2H), 1.56 (s, 9H), 0.90 (s, 9H), 0.06 (s, 6H). MS (ESI+): 734 (M+H)+, 756 (M+Na)+.

2-(4-(4-(4-(4-Amino styryl)-3-methoxystyryl)phenylsulfonyl)piperazin-1-yl)ethanol hydrochloride (compound 12): Compound 11 (66 mg, 0.09 mmol) was dissolved in 4 N HCl/dioxane (4.7 mL) and the reaction mixture was stirred at room temperature for 2 hrs. The resulting orange suspension was centrifuged at 300 r.c.f. for 10 mins. The pale yellow solution was decanted. The pallet was washed with hexanes (10 mL), centrifuged, and the clear solution decanted. The process was repeated twice, and the resulting light brown solid was dissolved in water and acetonitrile, and lyophilized overnight to yield 12 as a yellow solid (47 mg, 94% yield). 1H NMR (CD2Cl2) δ ppm: 7.92 (d, J=12 Hz, 2H), 7.79 (d, J=8.0 Hz, 2H), 7.80-7.69 (m, 5H), 7.50-7.29 (m, 8H), 3.95 (s, 3H), 3.76 (d, J=12 Hz, 2H), 3.74-3.69 (m, 2H), 3.57 (d, J=12 Hz, 2H), 3.25-3.18 (m, 4H), 2.74-2.68 (m, 2H). MS (ESI+): 542 (M+Na)+.

The invention claimed is:

1. A compound for detecting myelin-associated neuropathy in a subject wherein said compound is selected from the group consisting of:

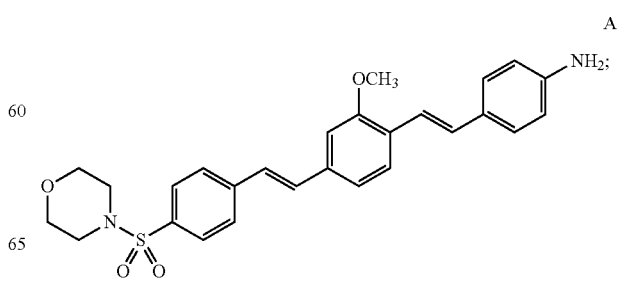

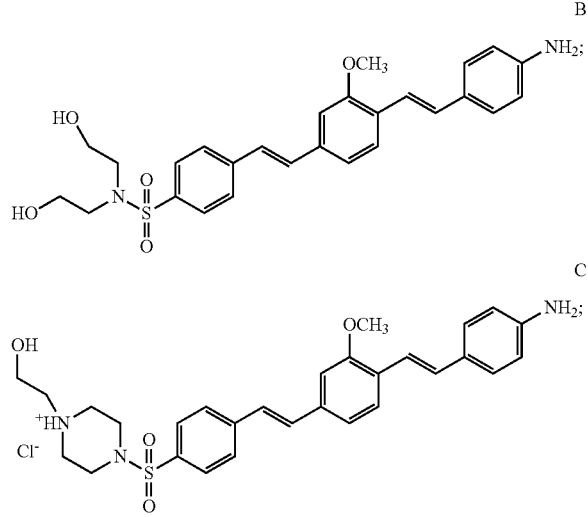

and a corresponding $^{19}$F-labeled derivative, radioisotope-labeled derivative, or salt thereof.

2. A method of detecting myelin-associated neuropathy comprising:
   identifying a subject at risk of or diagnosed with a myelin-associated neuropathy;
   administering to the subject an agent, wherein the agent comprises a compound of claim 1;
   determining myelination in the subject by detecting the agent present in the subject; and
   comparing the myelination in the subject with a control sample wherein a lower level of agent in the subject is indicative of a myelin-associated neuropathy.

3. The method of claim 2 wherein the administering comprises intravenous injection, intraperitoneal injection, subcutaneous injection, intramuscular injection, intrathecal injection, intracerebral injection, intracerebroventricular injection, intraspinal injection, or combinations thereof.

4. The method of claim 2 wherein the compound is a $^{19}$F-labeled derivative or a radioisotope-labeled derivative, and detecting is effected by gamma imaging, MRI, MRS, PET, CEST, PARACEST, or a combination thereof.

5. The method of claim 2 wherein the detecting is effected by applying a light source tuned to the spectral excitation characteristics of the compound, and observing the subject through an optical filter tuned to the spectral emission characteristics of the compound.

6. The method of claim 2 further comprising the step of quantifying the amount of the agent in the subject.

7. The method of claim 6 wherein the quantifying step comprises measuring radioactivity of the agent and wherein the agent comprises the radioisotope-labeled derivative of the compound or the radioisotope-labeled derivative of the salt of the compound.

8. The method of claim 2 wherein the myelin-associated neuropathy comprises multiple sclerosis, Guillain-Barré syndrome, leukodystrophies, metachromatic leukodystrophy, Refsum's disease, adrenoleukodystrophy, Krabbe's disease, phenylketonuria, Canavan disease, Pelizaeus-Merzbacher disease, Alexander's disease, diabetic neuropathy, chemotherapy-induced neuropathy, Alzheimer's disease, vascular dementia, dementia with Lewy bodies, or a combination thereof.

9. A method of imaging myelin basic protein in an open or minimally invasive surgical field comprising the steps of:
   contacting the surgical site with an agent, said agent comprising a compound of claim 1; and
   detecting the agent.

10. The method of claim 9 wherein the detecting is effected by applying a light source tuned to the spectral excitation characteristics of the compound, and observing the subject through an optical filter tuned to the spectral emission characteristics of the compound.

11. A method of quantifying the amount of myelin present in a tissue sample comprising:
   contacting the tissue sample with an agent wherein the agent comprises a compound of claim 1; and
   quantifying the amount of the agent present in the tissue sample by comparing to a baseline measurement of myelin basic protein in a control sample.

12. The method of claim 11 wherein the detecting is effected by fluorescence microscopy, laser-confocal microscopy, cross-polarization microscopy, autoradiography, or a combination thereof.

13. The method of claim 11 wherein the compound is a $^{19}$F-labeled derivative or a radioisotope-labeled derivative and detecting is effected by magnetic resonance imaging, magnetic resonance spectroscopy, or a combination thereof.

14. A kit for detecting myelin-associated neuropathy in a subject comprising:
   an agent wherein the agent comprises a compound of claim 1; and
   a pharmaceutical carrier.

15. The kit of claim 14 wherein the pharmaceutical carrier is a water-soluble organic solvent.

16. The kit of claim 15 wherein the pharmaceutical carrier further comprises a co-solvent, surfactant, buffer solution, stabilizer, preservative, or a combination thereof.

17. The kit of claim 14 wherein the pharmaceutical carrier comprises 5 to 20% (volume/volume) propylene glycol, 5 to 30% (weight to volume) 2-hydroxylpropyl-β-cyclodextrin, and 70 to 90% distilled deionized water (volume to volume).

18. The kit of claim 14 wherein the kit further comprises a multi-chambered vessel for storing the agent in a first chamber and a second pharmaceutical carrier in a second chamber.

* * * * *

UNITED STATES PATENT AND TRADEMARK OFFICE
CERTIFICATE OF CORRECTION

PATENT NO. : 8,658,129 B2  
APPLICATION NO. : 13/031349  
DATED : February 25, 2014  
INVENTOR(S) : Zhang et al.

Page 1 of 1

It is certified that error appears in the above-identified patent and that said Letters Patent is hereby corrected as shown below:

On the title page, item (75), under "Inventors", in Column 1, Line 5,
delete "Watervilet," and insert -- Watervliet, --, therefor.

In the Specification

In Column 5, Line 35, delete "cyclodextrans," and insert -- cyclodextrins, --, therefor.

In Column 18, Line 67, delete "may be then be" and insert -- may then be --, therefor.

In Column 20, Line 6, delete "Cyress" and insert -- Cypress --, therefor.

Signed and Sealed this
Twenty-seventh Day of May, 2014

Michelle K. Lee
*Deputy Director of the United States Patent and Trademark Office*